United States Patent [19]

Tracy

[11] Patent Number: 5,064,421
[45] Date of Patent: Nov. 12, 1991

[54] DISPOSABLE DIAPER WITH PADDED WAISTBAND AND LEGHOLES

[76] Inventor: Rhonda Tracy, 233 Grandview, Glen Ellyn, Ill. 60137

[21] Appl. No.: 516,473

[22] Filed: Apr. 30, 1990

Related U.S. Application Data

[63] Continuation-in-part of Ser. No. 93,681, Sep. 8, 1987, abandoned.

[51] Int. Cl.⁵ .................... A61F 13/15; A61F 13/20
[52] U.S. Cl. ................ 604/385.1; 604/386; 604/389
[58] Field of Search ............... 604/385.1, 385.2, 386, 604/387, 389, 390, 391

[56] References Cited

U.S. PATENT DOCUMENTS

| | | | |
|---|---|---|---|
| 1,329,119 | 1/1920 | George | 604/385.1 |
| 2,649,858 | 8/1953 | Bolt | 604/389 |
| 4,230,113 | 10/1980 | Mehta | 604/385.1 |
| 4,743,239 | 5/1988 | Cole | 604/385.1 |
| 4,753,645 | 6/1988 | Johnson | 604/385.1 |

Primary Examiner—Randall L. Green
Assistant Examiner—Paul Prebilic
Attorney, Agent, or Firm—Edward D. Gilhooly

[57] ABSTRACT

A disposable diaper having a front section, rear section, crotch portion, and a wasit band. A soft padding is provided on the waist band. Padding is also provided on the edge portions surrounding the leg holes.

5 Claims, 1 Drawing Sheet

DISPOSABLE DIAPER WITH PADDED WAISTBAND AND LEGHOLES

This is a continuation-in-part of my copending application Ser. No. 093,681, Sept. 8, 1987, now abandoned.

BACKGROUND OF THE INVENTION

1. Field of the Invention

This invention relates in general to a disposable diaper and more specifically, to a disposable diaper having a padded waistband and legholes.

2. Description of the Prior Art

Disposable diapers have largely replaced the common cloth diaper to be worn by infants and toddlers. Disposable diapers not only can be easily discarded, but are adjustable and convenient to attach and remove. Known diapers of the disposable variety are typically capable of effective retention of liquid and solid material without having to resort to protective covers as was required by cloth diapers. Although known disposable diaper designs are generally satisfactory, several problems haven arisen in their use. The waist band and border around the legholes of prior art disposable diapers are commonly an unprotected plastic band and the like. Such bands are uncomfortable when worn and often such material is stiff, and scratches and abrades an infant's skin. In addition, known waist bands and leg bands in disposable diapers do not provide an optimum barrier against leakage and seepage, which is so desirable.

SUMMARY OF THE INVENTION

It is therefore an objective of the invention to provide a disposable diaper having padded waist and leg areas. The padding as herein disclosed covers the plastic waistline band from inside to outside of the diaper when worn by the baby. The padding may be in the form of strips of soft pliable material, such as cotton and the like, and extends substantially around the waist. The soft padding protects the infant and toddler from scratches, irritations, and abrasions commonly inflicted by known diaper designs. The strip of padding further performs the added function of inhibiting leakage from within the diaper. The protection provided by the padding not only exists within the waist line portion of the diaper, but is also present at the top and outside of the diaper where the skin may overlap when worn.

The disposable diaper herein disclosed further includes strips of soft material, such as cotton and the like, at the edge portions of the diaper that surround the legs of the wearer to accomplish similar functions as the padding at the waist areas.

DESCRIPTION OF THE PREFERRED EMBODIMENT

Figure 1:
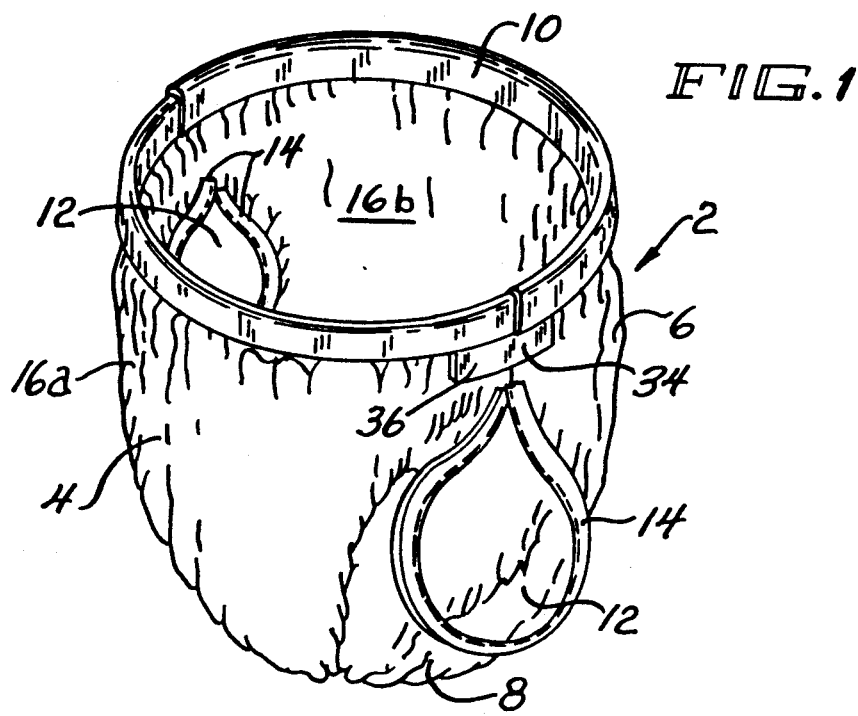
FIG. 1 is a perspective view, with parts of the waistline padding removed, of the disposable diaper of the invention.

Referring now to FIGS. 1-4, there is illustrated the disposable diaper with padded waistline and legholes of the invention, generally designated by reference numeral 2. In its closed configuration as it is worn in the form of FIG. 1, the diaper 2 is formed with a typical front section 4, a back section 6, a crotch area 8, and a top portion 10 forming an adjustable waistline construction. Leg holes 12 are defined by edge portions 14 of disposable diaper 2. The diaper 2 is formed in multiple superimposed sheets of material in front section 4, back section 6 and crotch area 8, including an outer liquid impervious outer sheet 16a and an inner liquid permeable sheet 16b as is well known. One or more layers 18 (FIGS. 3 and 4) of a liquid absorbent material, such as cotton, pulp and the like, is imposed between the outer sheet 16a and the inner sheet 16b as is conventional. The thickness of inner material 18 may be thickened in the crotch area 8 and elsewhere for greater liquid absorption.

Figure 2:
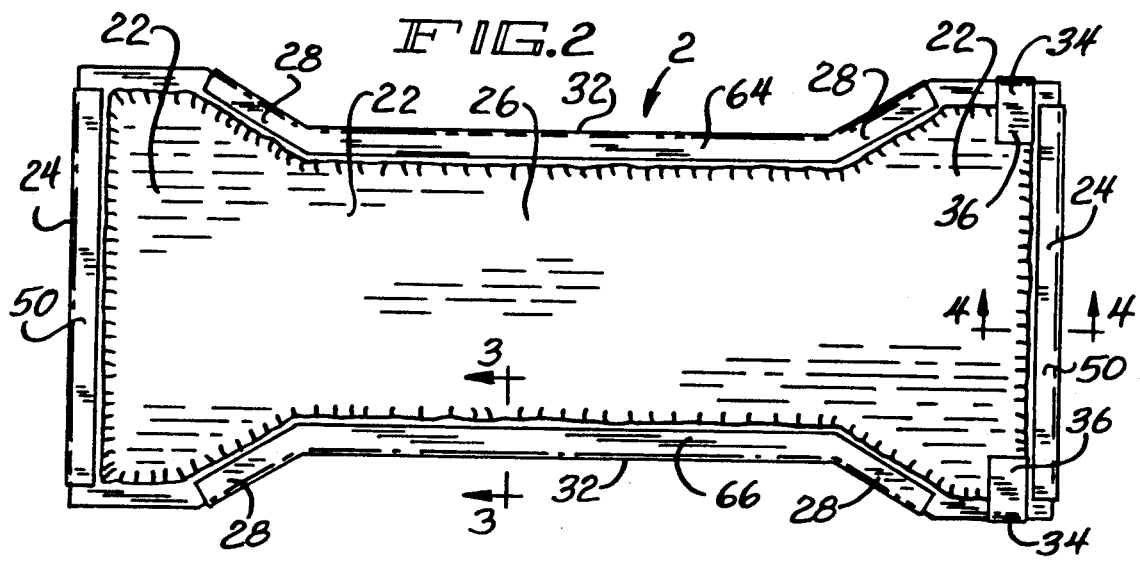
FIG. 2 is a rear plan view showing the inside of the diaper of FIG. 1 in a flat configuration.
Figure 3:
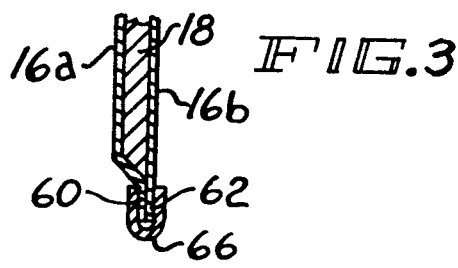
FIG. 3 is a partial end view, with parts in section, showing the portion of the diaper forming the legholes in the configuration of FIG. 1.

The diaper 2 in its flat configuration as shown in FIG. 2 is formed as a single body 20 having enlarged end portions 22 which terminate at edges 24 that form the top waist band portion 10 shown in FIG. 1. The intermediate section 26 of body 20 includes tapered edges 28 and a central section having opposed edges 32 that form the edge portions 14 of the leg holes 12. A pair of plastic adhesive strips 34 and the like having a detachable free end 36 are affixed on one enlarged end portion 22 of the body 20 to permit the diaper 2 to be adjustably affixed to the opposite end portion 22 to secure the diaper to the infant as in the configuration shown in FIG. 1.

Figure 4:
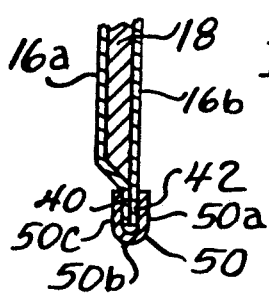
FIG. 4 is an end view, with parts in section, showing the edge portions of the diaper forming the waist band areas.

Referring now to FIGS. 1, 2, and 4, the waistline portion 10 is formed by border sections 40,42 of the inner and outer sheets 16a and 16b which are affixed together. The border sections 40, 42 are fabricated from a plastic material or similar material. A outer strip 50 of soft material in the form of a strip of cotton or other non-abrasive material is bent lengthwise over the border sections 40,42 of a plastic material and the like located on each of the enlarged sections 22 in FIG. 2 in affixed relationship by an suitable technique of attachment. The strip 50 forms surfaces 50a, 50b, and 50c that are respectively positioned from inside to outside of the diaper 2 so as to provide a soft cushion or pad substantially over the exposed surfaces of border sections 40,42 to protect the skin of the infant or toddler and provide an additional absorbent barrier to alleviate leakage. The strip 50 may be formed as a pair of strips to generally extend 360 degrees at the waist in the configuration of FIG. 1 (one of the strips 50 being cut away in FIG. 1 for illustrative purposes).

Referring again to FIGS. 1, 2, and 4, the edge portions 12 for leg holes 14 are similarly constructed as the waist band as previously described. The plastic borders 60,62 are affixed together (FIG. 3) and are covered in affixed relationship by strips 64, 66 of a soft material, such as cotton, to cover the exposed surfaces of borders 60,62 to serve the same function at leg holes 14 as soft strips 50 at the waist band.

What is claimed is:

1. A disposable diaper comprising
body means being formed as a single piece having two enlarged opposed end portions and a narrowed intermediate portion disposed between said opposed end portions, said body means being arranged to be worn by an individual, said opposed end portions each having an opposite edge portion, said body means including a layer of liquid absorbent material, waist band means being formed on said opposite edge portions of said opposed enlarged end portions and being in contact with said layer of absorbent material, said waist band means including a border section of plastic material covering said opposite edge portions of said body means, attachment means affixed to one of said opposed end portions and having members to be affixed to the other of said opposed end portions, said waist band means forming a substantially continuous waist band of predetermined extent to be positioned generally around the waist of the individual, said waist band means including external padding means extending along each of said opposite edge portions for generally covering the exposed surfaces of said waist band means, said padding means extending substantially the extent of said waist band means when worn by the individual, said padding means includes strips of material formed from a soft substance and, said strips of material covering only said border section of said waist band means for forming a soft surface for contact with the skin of the individual.

2. The disposable diaper according to claim 1 wherein said strips of material are folded lengthwise over said opposite edge portions of said opposite end portions.

3. The disposable diaper according to claim 1 wherein said intermediate portion includes opposite edge sections defining leg holes when said body means is worn, second padding means being provided over said edge sections of said intermediate portion to provide soft material in contact with the individual.

4. The disposable diaper of claim 3 wherein said second padding means is at least one soft strip of material affixed to each of said edge sections of said intermediate portion.

5. The disposable diaper of claim 4 wherein said at least one strip of material is lengthwise bent over each of said edge sections.

* * * * *